US012768982B2

(12) United States Patent
Gu et al.

(10) Patent No.: US 12,768,982 B2
(45) Date of Patent: Oct. 20, 2026

(54) MEASURING APPARATUS FOR CONCRETE STRUCTURE

(71) Applicant: SAMSUNG ELECTRONICS CO., LTD., Suwon-si (KR)

(72) Inventors: Jauk Gu, Suwon-si (KR); Eunho Lee, Suwon-si (KR); Changhyeon Kim, Suwon-si (KR); Youngdae Shim, Suwon-si (KR); Jinhoon Park, Suwon-si (KR)

(73) Assignees: SAMSUNG ELECTRONICS CO., LTD., Suwon-si (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 252 days.

(21) Appl. No.: 18/672,718

(22) Filed: May 23, 2024

(65) Prior Publication Data

US 2025/0123388 A1 Apr. 17, 2025

(30) Foreign Application Priority Data

Oct. 17, 2023 (KR) ........................ 10-2023-0138898

(51) Int. Cl.
*G01S 13/86* (2006.01)
*G01N 22/04* (2006.01)
(Continued)

(52) U.S. Cl.
CPC .............. *G01S 13/86* (2013.01); *G01N 22/04* (2013.01); *G01N 27/9046* (2013.01); *G01N 33/383* (2013.01); *G01S 13/885* (2013.01)

(58) Field of Classification Search
CPC ........ G01S 13/86; G01S 13/88; G01S 13/885; G01N 22/04; G01N 19/10; G01N 33/383; G01N 27/90–9093
See application file for complete search history.

(56) References Cited

U.S. PATENT DOCUMENTS 6,667,709 B1 * 12/2003 Hansen .................. G01S 13/88
367/128
9,625,403 B1 4/2017 Hussain et al.
(Continued)

FOREIGN PATENT DOCUMENTS

KR 10-1273626 B1 6/2013
KR 10-1846504 B1 4/2018
(Continued)

*Primary Examiner* — Matthew M Barker
(74) *Attorney, Agent, or Firm* — Sughrue Mion, PLLC

(57) ABSTRACT

A measuring apparatus for a concrete structure includes an eddy current sensor configured to contact the concrete structure; a ground penetrating radar (GPR) sensor configured to contact the concrete structure; at least one memory storing one or more instructions; and a controller operably connected to the eddy current sensor, the GPR sensor, and the at least one memory, wherein the one or more instructions, when executed by the controller, cause the apparatus to: provide a first input signal to the eddy current sensor and a second input signal to the GPR sensor, obtain a first moisture content of a portion of the concrete structure based on an output of the eddy current sensor, obtain a second moisture content of the portion of the concrete structure based on an output of the GPR sensor, and obtain a final moisture content of the portion of the concrete structure based on at least one of the first moisture content and the second moisture content.

13 Claims, 13 Drawing Sheets

(51) Int. Cl.

| | |
|---|---|
| ***G01N 27/90*** | (2021.01) |
| ***G01N 33/38*** | (2006.01) |
| ***G01S 13/88*** | (2006.01) |

(56) References Cited

U.S. PATENT DOCUMENTS

| | | | | |
|---|---|---|---|---|
| 10,352,883 | B2 * | 7/2019 | Krapf .................. | G01S 13/0209 |
| 2023/0400427 | A1 | 12/2023 | Choi et al. | |
| 2025/0180493 | A1 * | 6/2025 | Al-Qadi ................. | G01N 33/42 |

FOREIGN PATENT DOCUMENTS

| | | | |
|---|---|---|---|
| KR | 10-2021-0096856 | A | 8/2021 |
| KR | 10-2306993 | B1 | 9/2021 |
| KR | 10-2310099 | B1 | 10/2021 |
| KR | 10-2435577 | B1 | 8/2022 |
| KR | 10-2466333 | B1 | 11/2022 |
| KR | 10-2023-0052102 | A | 4/2023 |

* cited by examiner

MEASURING APPARATUS FOR CONCRETE STRUCTURE

CROSS-REFERENCE TO RELATED APPLICATION

This application is based on and claims the priority to Korean Patent Application No. 10-2023-0138898, filed on Oct. 17, 2023, in the Korean Intellectual Property Office, the entire disclosure of which is incorporated by reference herein for all purposes.

BACKGROUND

The disclosure relates to a measuring apparatus for a concrete structure.

Concrete is a mixture of cement and aggregates such as sand, gravel and the like, and is highly durable. It may therefore be used as a main material in civil engineering or construction. For inspection and maintenance of concrete structures as they age, testing that does not cause destruction or damage to the structure (i.e., non-destructive testing (NDT)) may be used. Specifically, when the concrete structure is a storage tank, such as a water tank or the like, various methods have been proposed to detect water leakage due to damage to a waterproofing material.

SUMMARY

Example embodiments are provide a measuring apparatus, including an eddy current sensor and a GPR sensor, that may improve the reliability of measurement results and provide early detection of water leaks in concrete structures by measuring moisture content and mechanical properties of concrete structures.

According to an aspect of an example embodiment, an apparatus for measuring a concrete structure, includes: an eddy current sensor configured to contact the concrete structure; a ground penetrating radar (GPR) sensor configured to contact the concrete structure; at least one memory storing one or more instructions; and a controller operably connected to the eddy current sensor, the GPR sensor, and the at least one memory, wherein the one or more instructions, when executed by the controller, cause the apparatus to: provide a first input signal to the eddy current sensor and a second input signal to the GPR sensor, obtain a first moisture content of a portion of the concrete structure based on an output of the eddy current sensor, obtain a second moisture content of the portion of the concrete structure based on an output of the GPR sensor, and obtain a final moisture content of the portion of the concrete structure based on at least one of the first moisture content and the second moisture content.

According to an aspect of an example embodiment, an apparatus for measuring a concrete structure, includes: an eddy current sensor including: a first coil configured to receive an alternating current (AC) input signal and to generate a first magnetic field based on the AC input signal, wherein the first magnetic field generates an eddy current in a portion of the concrete structure; and a second coil configured to generate an induced voltage signal based on the first magnetic field and a second magnetic field generated by the eddy current; a ground penetrating radar (GPR) sensor including: a GPR transmitter configured to receive an electromagnetic pulse input signal and transmit the electromagnetic pulse input signal toward the portion of the concrete structure; and a GPR receiver configured to receive an electromagnetic pulse reflection signal which is the electromagnetic pulse input signal reflected from an interface of the concrete structure; and a housing surrounding the eddy current sensor and the GPR sensor, wherein the housing includes a contact surface configured to contact the concrete structure, and the eddy current sensor and the GPR sensor are adjacent to the contact surface when the contact surface is in contact with the concrete structure.

According to an aspect of an example embodiment, an apparatus for measuring a concrete structure, includes: an eddy current sensor, the eddy current sensor including a first coil and a second coil; a ground penetrating radar (GPR) sensor, the GPR sensor including a GPR transmitter and a GPR receiver; at least one memory storing one or more instructions; and a controller operably connected to the eddy current sensor, the GPR sensor, and the at least one memory, wherein the one or more instructions, when executed by the controller, cause the apparatus to: provide an alternating current (AC) input signal to the first coil to cause the first coil to generate a first magnetic field, wherein the first magnetic field generates an eddy current in the concrete structure, provide an electromagnetic pulse input signal to the GPR transmitter, receive an induced voltage signal generated by the second coil, wherein the induced voltage signal is generated in response to the first magnetic field and a second magnetic field generated by the eddy current, control the GPR transmitter to transmit the electromagnetic pulse input signal toward the concrete structure, receive, through the GPR receiver, an electromagnetic pulse reflection signal, wherein the electromagnetic pulse reflection signal is reflected from an interface of the concrete structure, obtain an impedance of the second coil based on the induced voltage signal and the AC input signal, obtain a first moisture content of a portion of the concrete structure based on the impedance of the second coil, obtain a second moisture content of the portion of the concrete structure based on the electromagnetic pulse reflection signal, obtain a final moisture content of the portion of the concrete structure based on at least one of the first moisture content and the second moisture content, and obtain mechanical properties of the portion of the concrete structure based on the final moisture content.

BRIEF DESCRIPTION OF THE DRAWINGS

The above and other aspects, features, and advantages of the disclosure will be more clearly understood from the following detailed description, taken in conjunction with the accompanying drawings, in which.

DETAILED DESCRIPTION

Hereinafter, example embodiments will be described with reference to the accompanying drawings.

It will be understood that when an element is referred to as being "connected" with or to another element, it can be directly or indirectly connected to the other element, wherein the indirect connection may include "connection via a wireless communication network".

Also, when a part "includes" or "comprises" an element, unless there is a particular description contrary thereto, the part may further include other elements.

Throughout the description, when a member is "on" another member, this includes not only when the member is in contact with the other member, but also when there is another member between the two members.

Herein, the expressions "at least one of a, b or c" and "at least one of a, b and c" indicate "only a," "only b," "only c," "both a and b," "both a and c," "both b and c," and "all of a, b, and c."

It will be understood that, although the terms first, second, third, etc., may be used herein to describe various elements, is the disclosure should not be limited by these terms. These terms are only used to distinguish one element from another element.

As used herein, the singular forms "a," "an" and "the" are intended to include the plural forms as well, unless the context clearly indicates otherwise.

With regard to any method or process described herein, an identification code may be used for the convenience of the description but is not intended to illustrate the order of each step or operation. Each step or operation may be implemented in an order different from the illustrated order unless the context clearly indicates otherwise. One or more steps or operations may be omitted unless the context of the disclosure clearly indicates otherwise.

Figure 1:
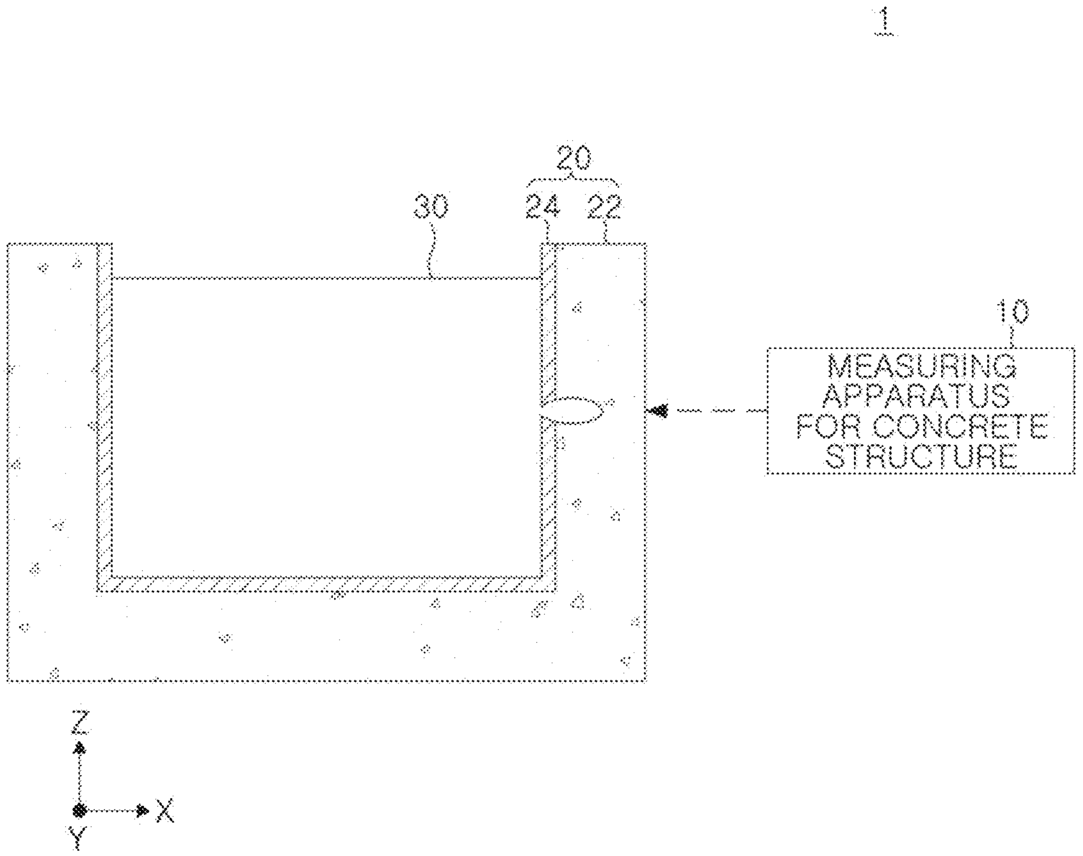
FIG. 1 is a diagram schematically illustrating a concrete structure measurement system according to an example embodiment.

FIG. 1 is a diagram schematically illustrating a concrete structure measurement system according to an example embodiment.

A concrete structure measurement system 1 may include a measuring apparatus for a concrete structure 10 and a concrete structure 20. FIG. 1 illustrates a concrete structure measurement system 1 of an example embodiment, and may be a diagram schematically illustrating a cross section of the measuring apparatus for a concrete structure 10 and the concrete structure 20.

In an example embodiment, the concrete structure 20 may have a cylindrical or rectangular shape, but embodiments of the disclosure are not limited thereto. The concrete structure 20 may have a certain area empty inside, and more specifically, the concrete structure 20 may correspond to a structure that stores a specific material 30.

In an example embodiment, a specific material 30 may be stored inside the concrete structure 20. The specific material 30 may correspond to ultrapure water (UPW) or waste water. For example, ultrapure water may be used in semiconductor manufacturing processes, and wastewater may be generated from a semiconductor manufacturing process. However, embodiments of the disclosure are not limited thereto.

The concrete structure 20 may include a concrete wall 22 and a waterproofing material 24. The concrete wall 22 may have a certain thickness and form the exterior of the concrete structure 20. The concrete wall 22 may maintain the structural stability of the concrete structure 20 even while the specific material 30 is stored in the concrete structure 20. For example, the thickness of the concrete wall 22 may be 1.5 m, but is not limited thereto.

In an example embodiment, the waterproofing material 24 may be applied to the interior of the concrete structure 20, and more specifically, the waterproofing material 24 may be applied to cover the entire inner surface of the concrete wall 22. The waterproofing material 24 may prevent specific materials 30 from penetrating into the concrete wall 22 and causing water leakage.

However, defects may occur in the waterproofing material 24 due to repeated storage and discharge of a specific material 30 in the concrete structure 20. For example, fine cracks may occur in the waterproofing material 24, and as a result, some of the stored specific material 30 may leak into the concrete wall 22.

The measuring apparatus for a concrete structure 10 of an example embodiment may determine whether the concrete structure 20 is leaking and the degree of water leakage by contacting one surface of the concrete structure 20 and measuring the moisture content and/or mechanical properties of the concrete structure 20. Therefore, without draining the specific material 30 stored inside the concrete structure 20 and opening the concrete structure 20 to directly measure the waterproofing material 24 or directly observe the waterproofing material 24 with the naked eye, the presence and extent of water leakage may be measured from the outside of the concrete structure 20. More specifically, water leakage in the concrete structure 20 may be determined without time and space constraints.

The measuring apparatus for a concrete structure 10 according to an example embodiment may include an eddy current sensor and a ground penetrating radar (GPR) sensor. By deriving the moisture content and mechanical properties of the concrete structure 20 using at least one of the eddy current sensor and the GPR sensor, the reliability of the measurement results of the measuring apparatus for a concrete structure 10 may be improved. For example, as the thickness of concrete that may be measured by the measuring apparatus for a concrete structure 10 of an example embodiment increases, leakage may be detected early before the leakage reaches the outermost layer of concrete.

Figure 2:
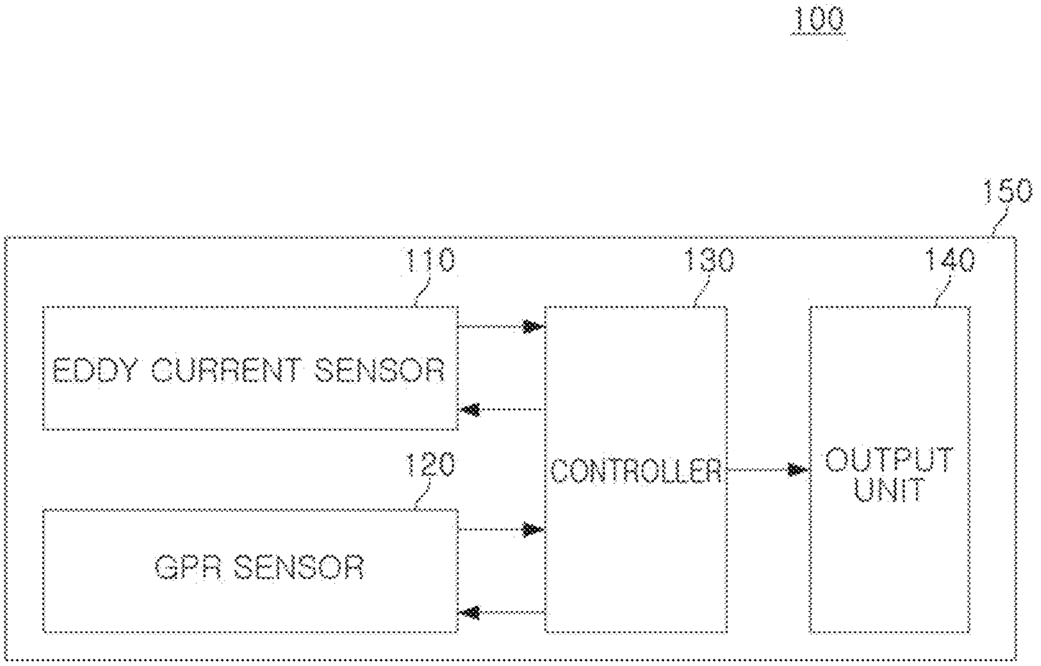
FIG. 2 is a block diagram schematically illustrating a measuring apparatus for a concrete structure according to an example embodiment.

FIG. 2 is a block diagram schematically illustrating a measuring apparatus for a concrete structure according to an example embodiment.

Referring to FIG. 2, the measuring apparatus for a concrete structure 100 according to an example embodiment may include an eddy current sensor 110, a GPR sensor 120, a controller 130, an output unit 140, and a housing 150. The housing 150 may have a shape surrounding the eddy current sensor 110, the GPR sensor 120, the controller 130, and the output unit 140, and the housing 150 may serve to protect the components 110-140 from external stimuli.

For example, the housing 150 may include a contact surface that directly contacts the concrete structure. The eddy current sensor 110 and the GPR sensor 120 may be disposed adjacently to the contact surface, and measurements may be made on some areas of the concrete structure adjacently to the contact surface. Therefore, the measuring apparatus for a concrete structure 100 may measure the final moisture content and/or mechanical properties of concrete through the contact surface.

The controller 130 in an example embodiment may control the eddy current sensor 110 and the GPR sensor 120. The controller 130 may apply an input signal to the eddy current sensor 110 and the GPR sensor 120, and more specifically, an alternating current input signal may be applied to the eddy current sensor 110 and an electromagnetic pulse input signal may be applied to the GPR sensor 120. The controller 130 may calculate the first moisture content using the output of the eddy current sensor 110 and calculate the second moisture content using the output of the GPR sensor 120. The controller 130 derives the final moisture content of the concrete structure using at least one of the first moisture content and the second moisture content, and the mechanical properties of concrete structures may be derived using the final moisture content.

The eddy current sensor 110 of an example embodiment may be in contact with a concrete structure. Eddy current sensor 110 may include a first coil and a second coil. While applying an alternating current input signal to the first coil, the controller 130 may detect an eddy current generated in the concrete structure and an induced voltage signal generated in the second coil by the alternating current input signal. The controller 130 may calculate the impedance of the second coil using an induced voltage signal and an alternating current input signal, and for example, the impedance of the second coil may be calculated by performing a Fast Fourier Transform on the induced voltage signal and the AC input signal. For example, the controller 130 may derive the first moisture content using the real part and the imaginary part of the impedance of the second coil. As another example, the controller 130 may derive the first moisture content using the phase of the impedance of the second coil. As another example, the controller 130 may derive the first moisture content using all the real part, imaginary part, and phase of the impedance of the second coil.

The GPR sensor 120 in an example embodiment may be in contact with a concrete structure. The GPR sensor 120 may include a transmitter and a receiver. The transmitter may transmit the electromagnetic pulse input signal applied by the controller 130 to the concrete structure. The receiver may receive and output an electromagnetic pulse reflection signal in which the electromagnetic pulse input signal is reflected from the interface of the concrete structure. As an example, the electromagnetic pulse reflection signal may have multiple peak values.

The controller 130 of an example embodiment may calculate the speed of the electromagnetic pulse reflection signal using the time between adjacent peak values among the plurality of peak values of the electromagnetic pulse reflection signal. The controller 130 may derive the permittivity of the concrete structure using the calculated speed, and the controller 130 may derive the second moisture content using the derived dielectric constant.

The controller 130 may derive the final moisture content using at least one of the first moisture content and the second moisture content. In addition, the mechanical properties of concrete structures may be derived using the final moisture content. Mechanical properties may include at least one of the elastic modulus and compressive strength of the concrete structure. Additionally, as in an example embodiment, the output unit 140 may output the final moisture content and mechanical properties of the concrete structure derived by the controller 130.

For example, the controller 130 may derive the average of the first moisture content and the second moisture content as the final moisture content. As another example, the controller 130 may derive one of the first moisture content and the second moisture content as the final moisture content. In an example embodiment, the output unit 140 may display numerical values representing the final moisture content and mechanical properties on the screen. Managers who maintain or repair concrete structures may use the displayed data to determine whether the concrete structure is leaking and the degree of leakage.

The measuring apparatus for a concrete structure 100 as an example of the disclosure may derive the final moisture content and/or mechanical properties of the concrete structure using at least one of the output of the eddy current sensor 110 and the output of the GPR sensor 120. More specifically, by measuring concrete structures using eddy current and ground penetrating radar (GPR), the reliability of the derived final moisture content and/or mechanical properties may be improved. Therefore, by accurately determining whether the concrete structure is leaking and the degree of water leakage, water leakage problems may be detected early before the water leakage progresses to the outermost layer of the concrete structure.

Figure 3:
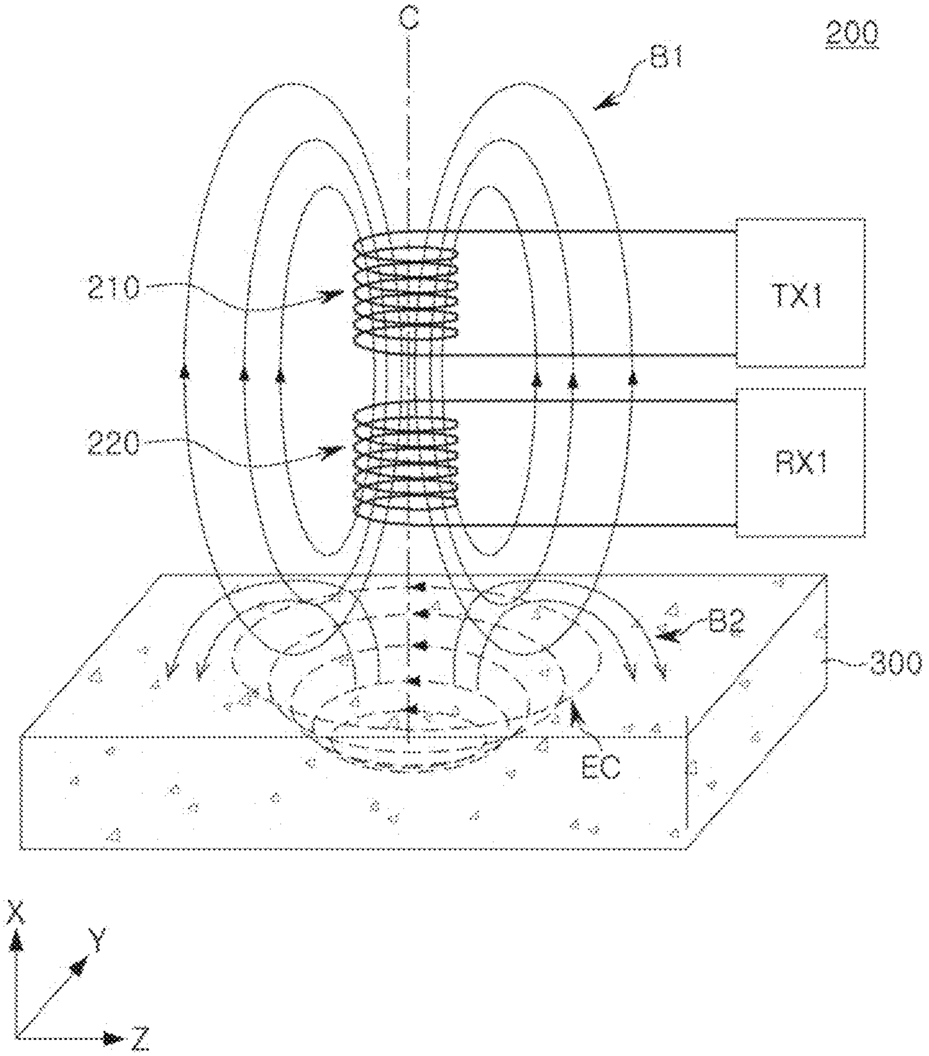
FIG. 3 is a diagram schematically illustrating an operation of an eddy current sensor according to an example embodiment.
Figure 4:
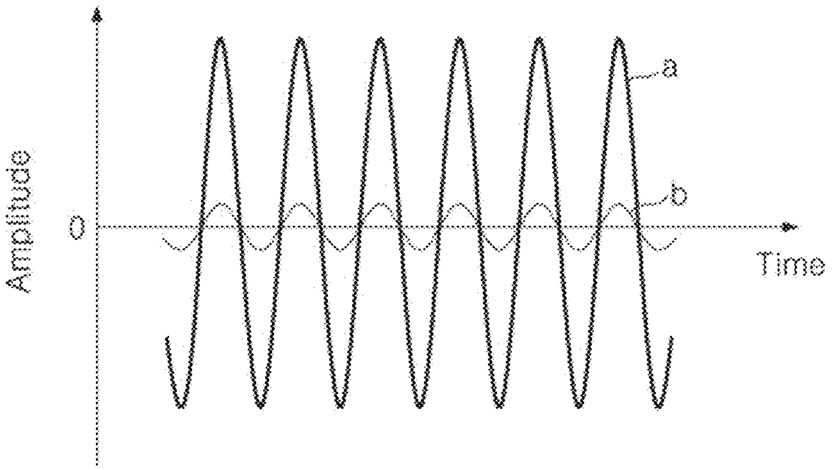
FIG. 4 is a diagram illustrating an output of an eddy current sensor according to an example embodiment.

FIG. 3 is a diagram schematically illustrating the operation of an eddy current sensor according to an example embodiment. FIG. 4 is a diagram illustrating the output of an eddy current sensor according to an example embodiment.

First, referring to FIG. 3, the eddy current sensor 200 may contact the concrete structure 300. More specifically, the measuring apparatus for a concrete structure may include a contact surface in contact with the concrete structure 300, and the eddy current sensor 200 may be disposed adjacently to the contact surface.

The eddy current sensor 200 may include a first coil 210 and a second coil 220. In an example embodiment, the first coil 210 and the second coil 220 may be arranged in a line along the X-axis (as shown in FIG. 3), which is perpendicular to the contact surface. More specifically, the second coil 220 may be disposed between the first coil 210 and the concrete structure 300 along the X-axis of FIG. 3. Additionally, the central axis C of the first coil 210 may align with the central axis C of the second coil 220.

For example, the eddy current sensor 200 may be connected to the controller of the measuring apparatus for a concrete structure. In an embodiment, the first transmitter TX1 and the first receiver RX1 may be included in the controller of the measuring apparatus for a concrete structure. More specifically, both ends of the first coil 210 of the eddy current sensor 200 may be connected to the first transmitter TX1, and both ends of the second coil 220 of the eddy current sensor 200 may be connected to the first receiver RX1.

In an example embodiment, the first transmitter TX1 of the controller may apply an input signal to the first coil 210, and the input signal may correspond to an alternating current input signal. Referring to FIG. 4, the AC input signal (b) may correspond to an AC voltage whose magnitude and direction changes with a constant period. For example, the AC input signal (b) may be an AC voltage in a high frequency band, and the AC input signal (b) may have a frequency in the megahertz (MHz) band.

Referring to FIG. 3, when an alternating current input signal flows through the first coil 210, a first magnetic field B1 may be generated around the first coil 210. The direction of the first magnetic field B1 may be determined according to Ampere's Right Hand Rule. For example, the first magnetic field B1 may be formed in a direction entering the concrete structure 300 in the X-axis of FIG. 3 at the position of the central axis C. The magnitude and direction of the first magnetic field B1 may change depending on the alternating current input signal flowing through the first coil 210.

In an example embodiment, the first magnetic field B1 may generate an eddy current EC in a certain area of the concrete structure 300. More specifically, an eddy current EC flowing in a concentric circle may be generated around the first magnetic field B1, which is a time-varying magnetic flux. Eddy current EC may correspond to alternating current. The direction of eddy current EC may be determined according to Lenz's Law, and the magnitude of eddy current EC may be determined according to Faraday's Law.

For example, as the first magnetic field B1 is formed in the direction entering the concrete structure 300 along the X-axis of FIG. 3 at the position of the central axis C, eddy current EC may flow counterclockwise on the top surface of the concrete structure 300. Additionally, the eddy current EC may be larger the closer it is to the top surface of the concrete structure 300. In an example embodiment, the eddy current EC may generate a second magnetic field B2 around the eddy current EC, and the direction of the second magnetic field B2 may be opposite to the direction of the first magnetic field B1. More specifically, the second magnetic field B2 may be formed in a direction coming from the concrete structure 300 along the X-axis of FIG. 3 at the position of the central axis C.

In an example embodiment, the first magnetic field B1 and the second magnetic field B2 may affect the second coil 220. The first magnetic field B1 and the second magnetic field B2 may induce a current flowing in the second coil 220. More specifically, according to Lenz's law and Faraday's law, the first magnetic field B1 and the second magnetic field B2, which are time-varying magnetic fluxes, may induce alternating current flowing in the second coil 220. Accordingly, the second coil 220 may output an induced voltage signal to the first receiver RX1 connected to both ends of the second coil 220, and the induced voltage signal may correspond to an alternating current signal.

Referring to FIG. 4, the induced voltage signal (a) may correspond to an alternating voltage whose magnitude and direction changes with a constant period. In an example embodiment, the period of the induced voltage signal (a) may coincide with the period of the alternating current input signal (b). The maximum value of the induced voltage signal (a) may be greater than the maximum value of the alternating current input signal (b). However, the disclosure is not limited thereto.

Figure 5:
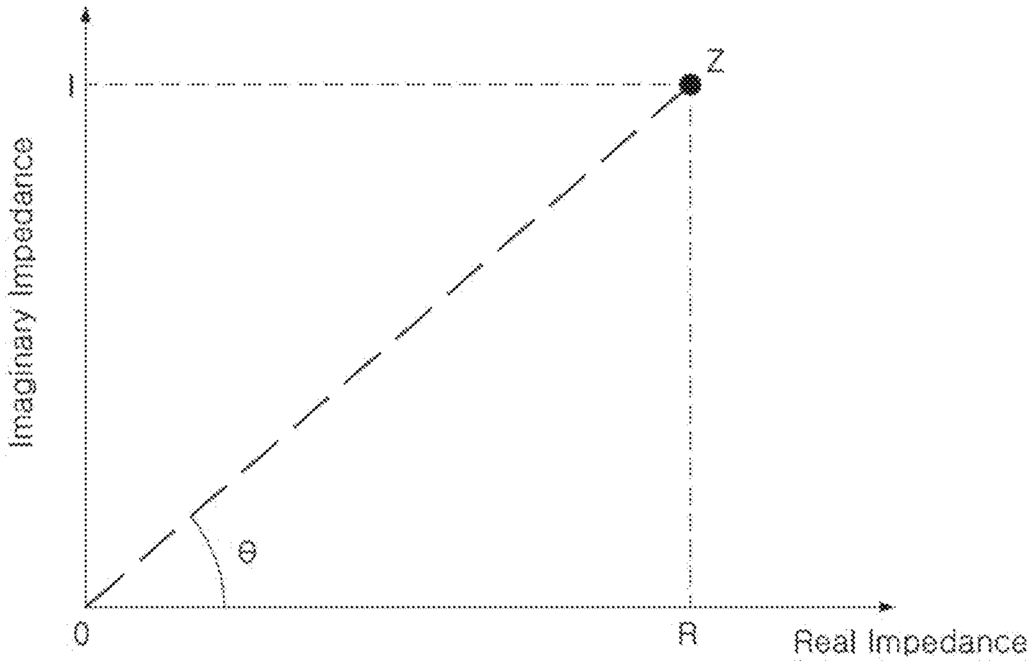
FIG. 5 is a diagram illustrating impedance of a second coil according to an example embodiment.
Figure 6:
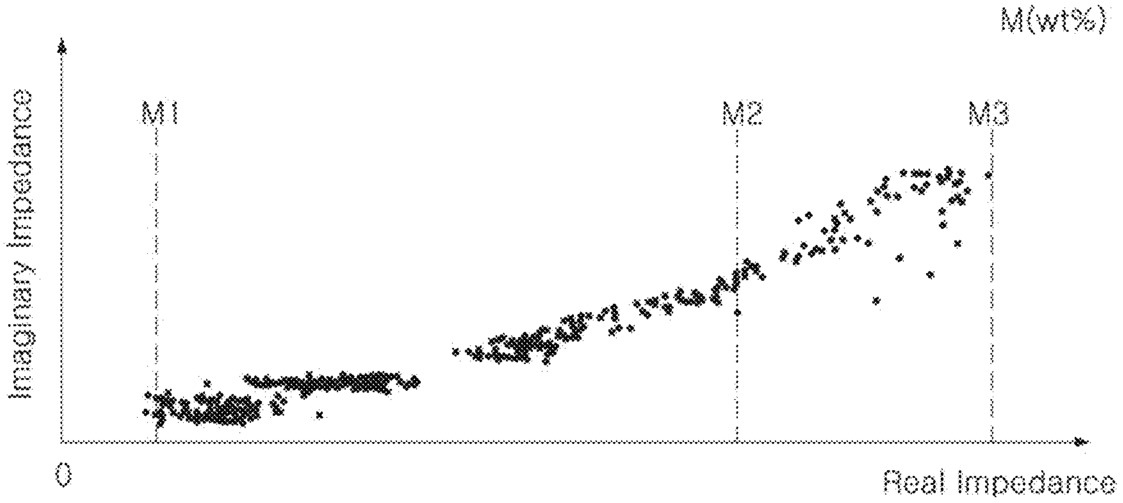
FIGS. 6, 7, and 8 are diagrams illustrating a relationship between impedance and moisture content of a second coil according to one or more example embodiments.
Figure 7:
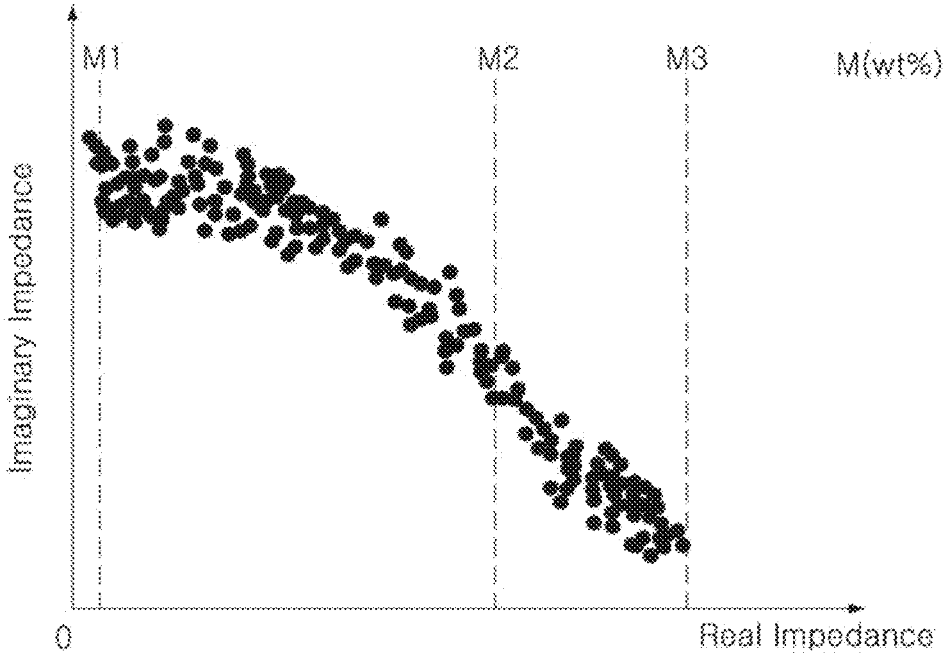
Figure 8:
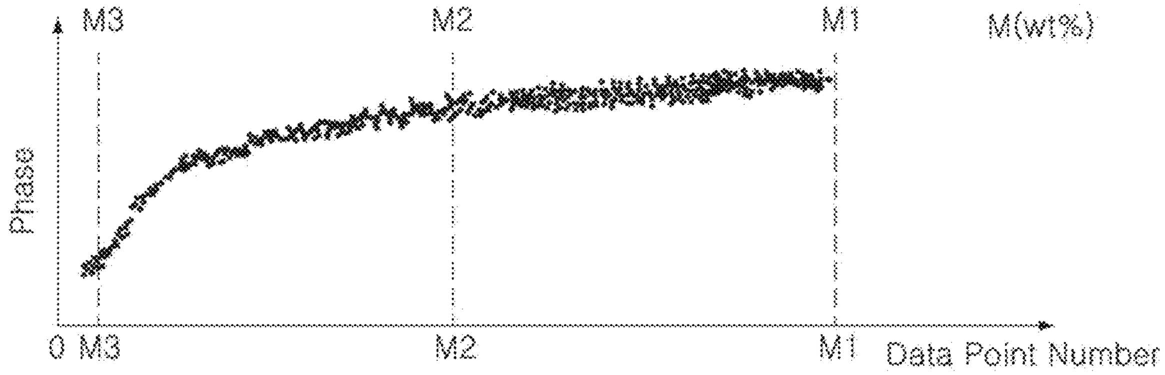

FIG. 5 is a diagram illustrating the impedance of the second coil according to an example embodiment. FIGS. 6 to 8 are diagrams illustrating the relationship between impedance and moisture content of the second coil according to example embodiments.

The measuring apparatus for a concrete structure may include an eddy current sensor and a controller. The eddy current sensor may include a first coil and a second coil, and the controller may calculate the first moisture content of the concrete structure using the output of the second coil. The controller of an example embodiment may detect an induced voltage signal generated in the second coil while applying an alternating current input signal to the first coil, and detailed embodiments may be similar to those described in FIGS. 3 and 4.

In an example embodiment, the controller may calculate the impedance of the second coil using an induced voltage signal and an alternating current input signal. In an embodiment, the controller may calculate the impedance of the second coil by performing a Fast Fourier Transform on the induced voltage signal and the AC input signal, but the disclosure is not limited thereto.

For example, the impedance of the second coil may correspond to a complex number. The impedance of the second coil may have magnitude and phase. The magnitude of the impedance of the second coil may be divided into a real part and an imaginary part. The phase of the second coil may correspond to the phase difference between the alternating current input signal and the induced voltage signal. An example embodiment of the alternating current input signal and the induced voltage signal may be similar to that described above in FIG. 4, but the disclosure is not limited thereto.

In an example embodiment illustrated in FIG. 5, the controller may calculate the impedance Z of the second coil using an induced voltage signal and an alternating current input signal. The magnitude of the impedance Z of the second coil may be divided into a real part R and an imaginary part I. The phase of the impedance Z of the second coil may correspond to θ, and for example, θ may correspond to an acute angle.

In an example embodiment, the controller may derive the first moisture content using the magnitude of the impedance of the second coil, and more specifically, the first moisture content may be derived using the real and imaginary parts of the impedance of the second coil.

FIGS. 6 and 7 may correspond to diagrams illustrating the relationship between the magnitude of the impedance of the second coil and the first moisture content according to example embodiments. According to the example embodiments illustrated in FIGS. 6 and 7, the first moisture content M of the concrete structure may be matched according to the magnitude of the impedance of the second coil, and the unit of the first moisture content M may correspond to mass percent (wt %). For example, the first moisture content M may be increased in the order of M1, M2, and M3, but embodiments of the disclosure are not limited thereto.

According to an example embodiment illustrated in FIG. 6, the larger the real part of the impedance of the second coil, the larger the imaginary part. More specifically, the larger the magnitude of the real and imaginary parts of the impedance of the second coil, the higher the first moisture content M of the area where the concrete structure is measured may be. Therefore, the larger the real part R and the imaginary part I of the impedance Z of the second coil illustrated in FIG. 5, the higher the first moisture content M may be derived.

According to an example embodiment illustrated in FIG. 7, the larger the real part of the impedance of the second coil, the smaller the imaginary part. More specifically, the larger the real part of the impedance of the second coil and the smaller the imaginary part, the higher the first moisture content M of the area where the concrete structure is measured may be. Therefore, the larger the real part R of the impedance Z of the second coil illustrated in FIG. 5 and the smaller the imaginary part I, the higher the first moisture content M may be derived.

In another embodiment, the controller may derive the first moisture content using the phase of the impedance of the second coil.

FIG. 8 may correspond to a diagram illustrating the relationship between the phase of the impedance of the second coil and the first moisture content according to an example embodiment. According to an example embodiment illustrated in FIG. 8, the first moisture content M of the concrete structure may be matched according to the phase of the impedance of the second coil, and the unit of the first moisture content M may correspond to mass percent (wt %). For example, the first moisture content M may be increased in the order of M1, M2, and M3, but embodiments of the disclosure are not limited thereto.

According to an example embodiment illustrated in FIG. 8, the smaller the phase of the impedance of the second coil, the higher the first moisture content M of the area where the concrete structure was measured. Therefore, the smaller the phase θ of the impedance Z of the second coil of the example embodiment illustrated in FIG. 5, the higher the first moisture content M may be derived.

The measuring apparatus for a concrete structure according to an example embodiment may derive the first moisture content through an eddy current sensor. The input alternating current signal applied to the eddy current sensor may have a frequency in the MHz band, and accordingly, the first moisture content may be measured not only on the outer part of the concrete structure but also at a specific depth. More specifically, a determination of whether there is a water leak may be made early by using the first moisture content measured before the water leak progresses to the outermost part of the concrete.

Figure 9:
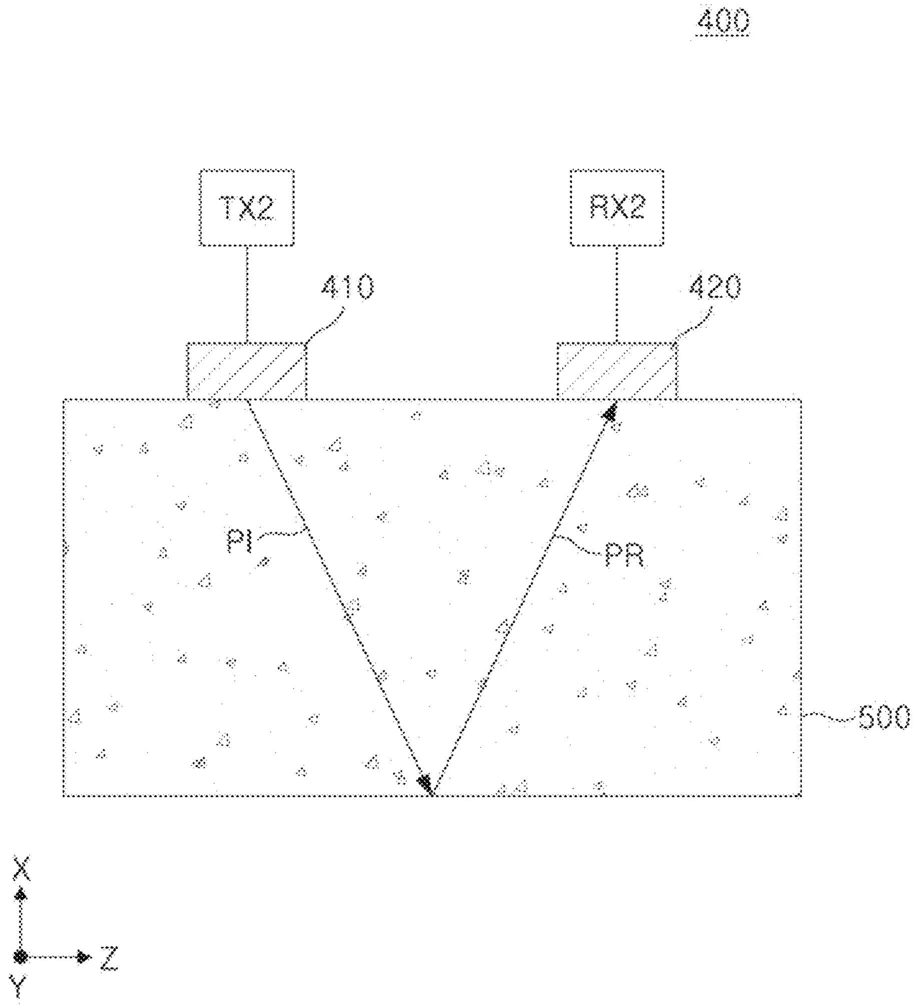
FIG. 9 is a diagram schematically illustrating an operation of a GPR sensor according to an example embodiment.
Figure 10:
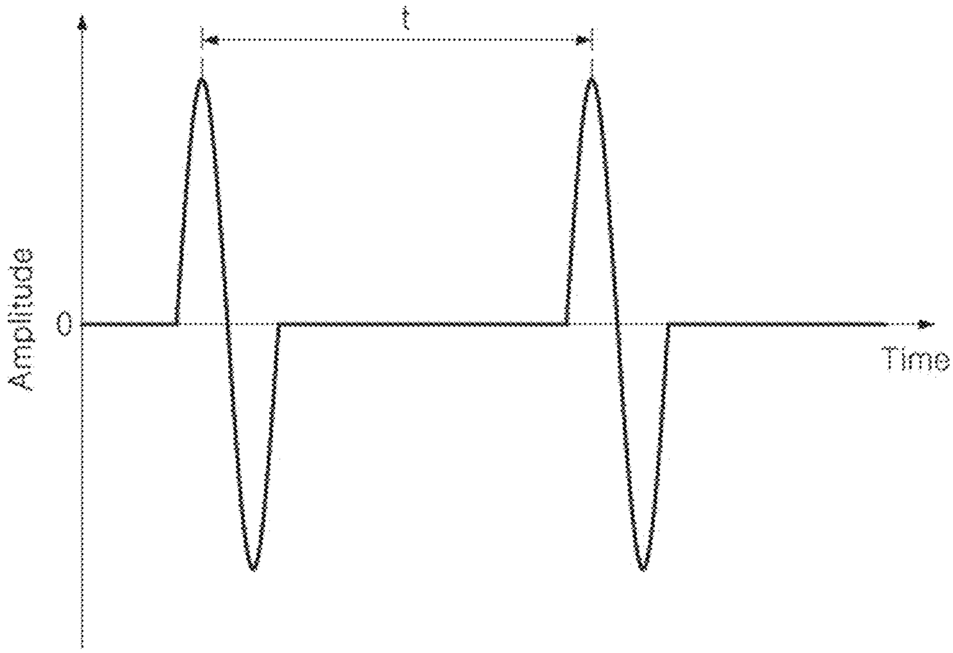
FIG. 10 is a diagram illustrating an output of a GPR sensor according to an example embodiment.

FIG. 9 is a diagram schematically illustrating the operation of a GPR sensor according to an example embodiment. FIG. 10 is a diagram illustrating the output of a GPR sensor according to an example embodiment.

First, referring to FIG. 9, the GPR sensor 400 may contact the concrete structure 500. More specifically, the measuring apparatus for a concrete structure may include a contact surface in contact with the concrete structure 500, and the GPR sensor 400 may be disposed adjacently to the contact surface.

The GPR sensor 400 may include a GPR transmitter 410 and a GPR receiver 420. In an example embodiment, the GPR transmitter 410 and the GPR receiver 420 may be arranged in a row along the Z-axis of FIG. 9 parallel to the contact surface. More specifically, the GPR transmitter 410 and the GPR receiver 420 may be arranged at regular intervals based on the Z axis of FIG. 9.

For example, the GPR sensor 400 may be connected to the controller of a measuring apparatus for a concrete structure. In an embodiment, the second transmitter TX2 and the second receiver RX2 may be included in the controller of the measuring apparatus for a concrete structure. More specifically, the GPR transmitter 410 may be connected to the second transmitter TX2, and the GPR receiver 420 may be connected to the second receiver RX2.

In an example embodiment, the second transmitter TX2 of the controller may apply an input signal to the GPR transmitter 410, and the input signal may correspond to an electromagnetic pulse input signal PI. As an example, the electromagnetic pulse input signal PI may have a frequency in the megahertz (MHz) to gigahertz (GMz) band.

Referring to FIG. 9, the GPR transmitter 410 may transmit the electromagnetic pulse input signal PI received from the controller to the concrete structure 500. In an embodiment, the electromagnetic pulse input signal PI may have an acute angle of incidence with respect to the interface of the concrete structure 500. The electromagnetic pulse input signal PI may be reflected from the interface of the concrete structure 500, and may be an electromagnetic pulse reflection signal PR. In an example embodiment, the electromagnetic pulse reflection signal PR may be received through the GPR receiver 420 and output to the controller (e.g., controller 130). For example, the wavelength, speed, and frequency of the electromagnetic pulse input signal PI and the electromagnetic pulse reflection signal PR may be the same.

Referring to FIG. 10, the electromagnetic pulse reflection signal may have a plurality of peak values. The controller may receive an electromagnetic pulse reflection signal from the GPR receiver. The controller may calculate the speed (v) of the electromagnetic pulse reflection signal using the time (t) between adjacent peak values among the plurality of peak values of the electromagnetic pulse reflection signal. More specifically, the speed (v) of the electromagnetic pulse reflection signal may be calculated using the time (t) between adjacent peak values and the thickness of the concrete structure.

Concrete structures may have different dielectric constants (ε) and velocities (v) of electromagnetic pulse reflection signals depending on moisture content. Therefore, by calculating the speed (v) of the electromagnetic pulse reflection signal, the dielectric constant (ε) of the concrete structure may be derived. For example, the dielectric constant (ε) of the concrete structure and the speed (v) of the electromagnetic pulse reflection signal may satisfy Equation 1. The controller may derive the second moisture content using the calculated dielectric constant (ε), and at this time, the characteristics of concrete with different dielectric constants depending on the moisture content may be used.

$$v = \frac{1}{\sqrt{\mu \times \varepsilon}} \quad \text{Equation 1}$$

In an embodiment, the permeability (u) of the concrete structure may be calculated using the vacuum permeability (μ0) and the relative permeability (μs) of the concrete structure, and more specifically, Equation 2 may be satisfied. For example, the relative permeability (μs) of a concrete structure may have a value close to 1.

$$\mu = \mu 0 \times \mu s \quad \text{Equation 2}$$

A measuring apparatus for a concrete structure according to an example embodiment may derive the final moisture content of the concrete structure, using at least one of the first moisture content derived through the eddy current sensor and the second moisture content derived through the GPR sensor. More specifically, by simultaneously applying the eddy current sensor and the GPR sensor, the reliability of the final moisture content derived may be improved. Therefore, the accuracy in determining whether a concrete structure is leaking may be improved.

Additionally, the measuring apparatus for a concrete structure according to an example embodiment may derive the mechanical properties of the concrete structure using the derived final moisture content. For example, the mechanical properties of a concrete structure may include at least one of elastic modulus and compressive strength. More specifically, by evaluating the deterioration of the physical properties of the concrete structure due to water leakage using the mechanical properties of the concrete structure, the accuracy of determining whether a concrete structure is leaking and the degree of leakage may be improved.

Figure 11:
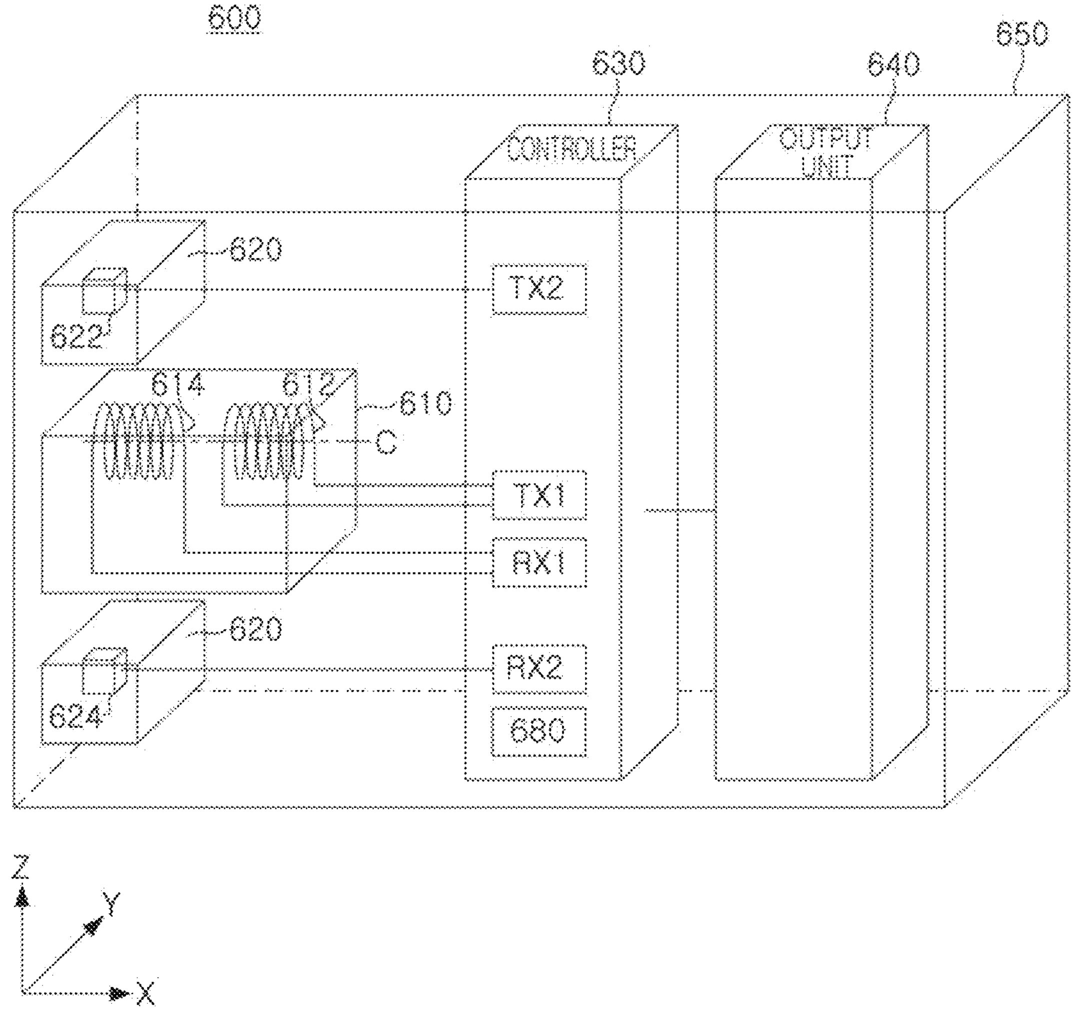
FIG. 11 is a diagram schematically illustrating a structure of a measuring apparatus for a concrete structure according to an example embodiment.

FIG. 11 is a diagram schematically illustrating the structure of a measuring apparatus for a concrete structure according to an example embodiment.

Referring to FIG. 11, the measuring apparatus for a concrete structure 600 according to an example embodiment may include an eddy current sensor 610, a GPR sensor 620, a controller 630, an output unit 640, and a housing 650. When compared to the measuring apparatus for a concrete structure 100 of FIG. 2, the measuring apparatus for a concrete structure 600 of FIG. 11 may correspond to the eddy current sensor 610 and the GPR sensor 620 specifically illustrated, and detailed embodiments may be similar to those described in FIG. 2.

In an example embodiment, the housing 650 may include a contact surface that directly contacts the concrete structure. The eddy current sensor 610 and the GPR sensor 620 may be disposed adjacently to the contact surface, and measurements may be made on some areas of the concrete structure adjacently to the contact surface. More specifically, the eddy current sensor 610 and the GPR sensor 620 may be arranged in a line in a first direction (Z-axis direction in FIG. 11) parallel to the contact surface.

The eddy current sensor 610 of an example embodiment may include a first coil 612 and a second coil 614. For example, the first coil 612 and the second coil 614 may be arranged in a line in a second direction (X-axis in FIG. 11) perpendicular to the contact surface. More specifically, the second coil 614 may be disposed between the first coil 612 and the housing 650 in the second direction. Additionally, the central axis C of the first coil 612 may align with the central axis C of the second coil 614, and the central axis C may be parallel to the second direction.

In an example embodiment, the eddy current sensor 610 may be connected to the controller 630. At this time, the first transmitter TX1 and the first receiver RX1 may be included in the controller 630. More specifically, both ends of the first coil 612 are connected to the first transmitter TX1, and both ends of the second coil 614 may be connected to the first receiver RX1. In an embodiment, the controller 630 may include a memory 680 configured to store data and instructions, including the library data described below.

For example, the first transmitter TX1 may apply an alternating current input signal to the first coil 612 as an input signal. When an alternating current input signal flows through the first coil 612, a first magnetic field may be generated around the first coil 612, the first magnetic field may generate an eddy current and a second magnetic field. In an example embodiment, the first magnetic field and the second magnetic field may induce a current flowing in the second coil 614, and the second coil 614 may output an induced voltage signal to the first receiver RX1 connected to both ends of the second coil 614.

The GPR sensor 620 in an example embodiment may include a GPR transmitter 622 and a GPR receiver 624. For example, the GPR transmitter 622 and the GPR receiver 624 may be arranged in a line in a first direction (Z-axis in FIG. 11) parallel to the contact surface, and a certain distance may be provided between the GPR transmitter 622 and the GPR receiver 624. More specifically, the eddy current sensor 610 may be disposed between the GPR transmitter 622 and the GPR receiver 624.

In an example embodiment, the GPR sensor 620 may be connected to the controller 630. At this time, the second transmitter TX2 and the second receiver RX2 may be included in the controller 630. More specifically, the GPR transmitter 622 may be connected to the second transmitter TX2, and the GPR receiver 624 may be connected to the second receiver RX2.

For example, the second transmitter TX2 may apply an electromagnetic pulse input signal to the GPR transmitter 622 as an input signal. The GPR transmitter 622 may transmit the received electromagnetic pulse input signal to the concrete structure. The GPR receiver 624 may receive, and output to the controller 630, an electromagnetic pulse reflection signal in which the electromagnetic pulse input signal is reflected from the interface of the concrete structure.

In an example embodiment, the controller 630 may calculate the impedance of the second coil using the induced voltage signal and the alternating current input signal received by the first receiver RX1, and the controller 630 may derive the first moisture content of the concrete structure using the impedance of the second coil. Additionally, the controller 630 may derive the second moisture content of the concrete structure using the electromagnetic pulse reflection signal received by the second receiver RX2.

The controller 630 of an example embodiment may derive the final moisture content using at least one of the first moisture content and the second moisture content, and the mechanical properties of concrete structures may be derived using the final moisture content. At this time, the mechanical properties may include at least one of the elastic modulus and compressive strength of the concrete structure.

In an example embodiment, the controller 630 may derive the average of the first moisture content and the second moisture content as the final moisture content. More specifically, when both the first moisture content and the second moisture content are within the error range, the controller 630 may derive the average of the first moisture content and the second moisture content as the final moisture content. In another embodiment, the controller 630 may derive one of the first moisture content and the second moisture content as the final moisture content. More specifically, when one of the first moisture content and the second moisture content is outside the error range, the controller 630 may derive the moisture content that does not exceed the error range as the final moisture content.

More specifically, concrete structures may be designed with different types and ratios of materials depending on the purpose. Concrete structures may have different properties depending on the design thereof. More specifically, each concrete structure may have different computable data that can be calculated based on the moisture content. For example, the computable data may correspond to a library for the impedance of the second coil and the speed of the electromagnetic pulse reflection signal. In an example embodiment, detailed embodiments of the library of the impedance of the second coil may be similar to those described in FIGS. 6 to 8, but embodiments of the disclosure are not limited thereto.

When at least one of the calculated impedance of the second coil and the speed of the electromagnetic pulse reflection signal does not match the data stored in the library, the controller 630 of an example embodiment may determine whether the value is within an error range, and the error range may be a preset value. For example, the controller 630 may determine whether the first moisture content and the second moisture content correspond to values within the error range for the library moisture content.

More specifically, the controller 630 determines the closest library data among the data stored in the library for each of the impedance of the second coil and the speed of the electromagnetic pulse reflection signal, and the corresponding library moisture contents may be derived respectively. For example, when the error range of the first moisture content is set to 5%, the controller 630 may determine that the first moisture content is outside the error range if the first moisture content is 7% greater than the library moisture content, and may determine that the first moisture content is within the error range if the first moisture content is 2% smaller than the library moisture content. However, embodiments of the disclosure are not limited thereto.

Therefore, when both the first moisture content and the second moisture content are within the error range, the controller 630 may derive the average of the first moisture content and the second moisture content as the final moisture content. When at least one of the first moisture content and the second moisture content is outside the error range, the controller 630 may derive the value within the error range among the first moisture content and the second moisture content as the final moisture content. In addition, when both the first moisture content and the second moisture content are outside the error range, the controller 630 may output a message requesting remeasurement to the output unit 640 without deriving the final moisture content.

In an example embodiment, the measuring apparatus for a concrete structure 600 is capable of measuring from the outside of the concrete structure, and thus may measure the concrete structure without draining or opening the concrete structure. More specifically, water leakage in concrete structures may be determined without spatial or temporal constraints. In addition, by deriving the moisture content and mechanical properties of the concrete structure using the outputs of the eddy current sensor 610 and the GPR sensor 620, the reliability of determining whether there is a water leak and the degree of water leakage may be improved.

Figure 12:
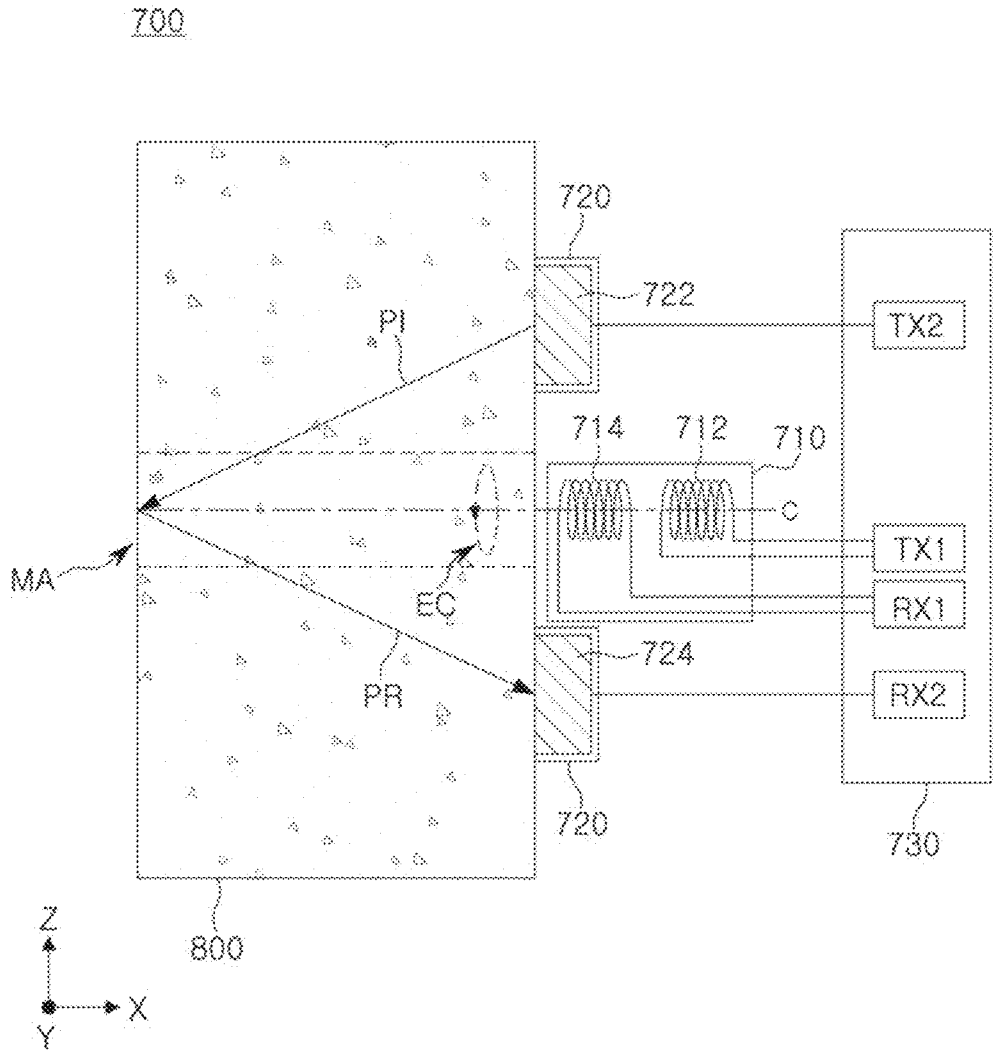
FIG. 12 is a diagram schematically illustrating an eddy current sensor and a GPR sensor according to an example embodiment.

FIG. 12 is a diagram schematically illustrating an eddy current sensor and a GPR sensor according to an example embodiment.

In an example embodiment, the measuring apparatus for a concrete structure 700 may include an eddy current sensor 710, a GPR sensor 720, a controller 730, an output unit, and a housing. The eddy current sensor 710 may include a first coil 712 and a second coil 714, and the GPR sensor 720 may include a GPR transmitter 722 and a GPR receiver 724. The controller 730 may include first and second transmitters TX1 and TX2 and first and second receivers RX1 and RX2. The housing surrounds the eddy current sensor 710 and the GPR sensor 720, and may include a contact surface in contact with the concrete structure 800.

The measuring apparatus for a concrete structure 700 may measure the concrete structure 800 by contacting the outside of the side of the concrete structure 800, and the measuring apparatus for a concrete structure 700 may measure the concrete structure 800 through the contact surface. More specifically, the eddy current sensor 710 and the GPR sensor 720 may be disposed adjacently to the contact surface, and the eddy current sensor 710 and the GPR sensor 720 may measure a partial area MA of the concrete structure 800 adjacently to the contact surface.

An example embodiment illustrated in FIG. 12 may correspond to a simplified illustration of the eddy current sensor 710 and the GPR sensor 720 that contact the concrete structure 800 and measure the concrete structure 800. For example, the eddy current sensor 710 and the GPR sensor 720 may be arranged in a line in a first direction (Z-axis direction in FIG. 12) parallel to the contact surface.

In the eddy current sensor 710 in an example embodiment, the first coil 712 and the second coil 714 may be arranged in a line in a second direction (X-axis in FIG. 12) perpendicular to the contact surface. More specifically, the second coil 714 may be disposed between the first coil 712 and the concrete structure 800 in the second direction. Additionally, the central axis C of the first coil 712 may align with the central axis C of the second coil 714, and the central axis C may be parallel to the second direction.

In the GPR sensor 720 according to an example embodiment, the GPR transmitter 722 and the GPR receiver 724 may be arranged in a line in a first direction, and a certain distance may be provided between the GPR transmitter 722 and the GPR receiver 724. More specifically, the eddy current sensor 710 may be disposed between the GPR transmitter 722 and the GPR receiver 724.

In the eddy current sensor 710 of an example embodiment, both ends of the first coil 712 are connected to the first transmitter TX1, and both ends of the second coil 714 may be connected to the first receiver RX1. The first transmitter TX1 may apply an alternating current input signal to the first coil 712. While an alternating current input signal is input to the first coil 712, eddy currents EC may occur in the concrete structure 800, the second coil 714 may output an induced voltage signal generated by an alternating current input signal and an eddy current EC. For example, eddy currents EC may be generated in certain areas of the outside adjacent concrete structure 800, and the central axis of the eddy current EC may align with the central axis C of the first and second coils 712 and 714.

In the GPR sensor 720 according to an example embodiment, the GPR transmitter 722 may be connected to the second transmitter TX2, and the GPR receiver 724 may be connected to the second receiver RX2. The second transmitter TX2 may apply an electromagnetic pulse input signal PI to the GPR transmitter 722. The GPR transmitter 722 may transmit the applied electromagnetic pulse input signal PI to the concrete structure 800, and the GPR receiver 724 may receive, and output to the controller 730, an electromagnetic pulse reflection signal PR in which the electromagnetic pulse input signal PI is reflected from the interface of the concrete structure 800. For example, the point where the electromagnetic pulse input signal PI is reflected may be located on the central axis C of the first and second coils 712 and 714.

According to an example embodiment, the controller 730 may derive the first moisture content of a partial area MA of the concrete structure using the impedance of the second coil 714 calculated using the induced voltage signal and the alternating current input signal, and the second moisture content of the partial area MA may be derived using the electromagnetic pulse reflection signal PR. The controller 730 may derive the final moisture content using at least one of the first moisture content and the second moisture content, and the mechanical properties of concrete structures may be derived using the final moisture content.

The final moisture content and mechanical properties may be output to the output unit of the measuring apparatus for a concrete structure 700. According to an example embodiment, by comparing the final moisture content and mechanical properties with reference values, whether there is water leakage and the degree of water leakage in a certain area MA of the concrete structure 800 may be determined. More specifically, early action may be taken by detecting water leakage before it progresses to the outermost part of the concrete structure 800.

Figure 13:
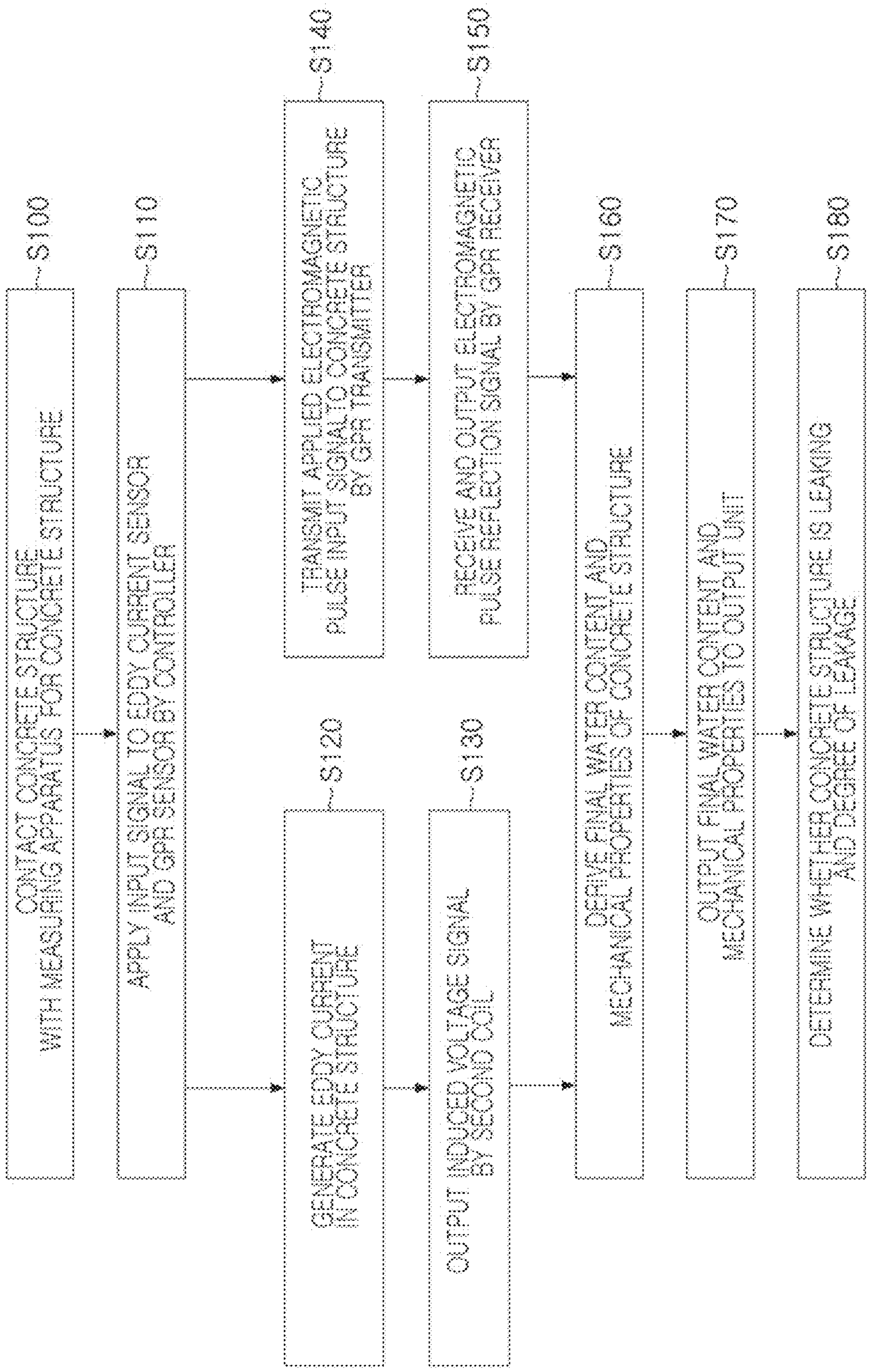
FIG. 13 is a flowchart illustrating an operation of a measuring apparatus for a concrete structure according to an example embodiment.

FIG. 13 is a flowchart illustrating the operation of the measuring apparatus for a concrete structure according to an example embodiment.

In an example embodiment, a measuring apparatus for a concrete structure may include an eddy current sensor, a GPR sensor, a controller, and an output unit. A measuring apparatus for a concrete structure may measure a concrete structure from the outside of the concrete structure. The eddy current sensor may include a first coil and a second coil, and the GPR sensor may include a GPR transmitter and a GPR receiver. The controller may control the eddy current sensor and the GPR sensor, and the output unit may output the results derived by the controller.

To determine whether the concrete structure is leaking and the degree of water leakage, the measuring apparatus for a concrete structure may first be brought into contact with the concrete structure (S100). More specifically, the measuring surface of the measuring apparatus for a concrete structure may be brought into contact with the concrete structure. Therefore, the eddy current sensor and the GPR sensor may be in contact with the concrete structure at the same time.

The controller may apply an input signal to the eddy current sensor and the GPR sensor (S110). The controller may apply an alternating current input signal as an attractive signal to the eddy current sensor, and more specifically, an alternating current input signal may be applied to the first coil. The controller may apply an electromagnetic pulse input signal as an input signal to the GPR sensor, and more specifically, an electromagnetic pulse input signal may be applied to the GPR transmitter. However, embodiments of the disclosure are not limited thereto, and in another embodiment, the input signal may be sequentially applied to the eddy current sensor and the GPR sensor.

When an alternating current input signal is applied to the first coil, eddy currents may be generated in the concrete structure (S120). More specifically, when an alternating current input signal flows through the first coil, a first magnetic field may be generated around the first coil, the magnitude and direction of the first magnetic field may change depending on the alternating current input signal flowing in the first coil.

The first magnetic field may generate eddy currents that flow in concentric circles in a certain area of the concrete structure. The eddy current may generate a second magnetic field around the eddy current. The first magnetic field and the second magnetic field may generate alternating current in the second coil. Therefore, the second coil may output an induced voltage signal (S130).

More specifically, while the controller applies an alternating current input signal to the first coil, the induced voltage signal generated in the second coil by the eddy current generated in the concrete structure and the alternating current input signal may be detected. Detailed embodiments may be similar to those described in FIG. 3.

The GPR transmitter may transmit the applied electromagnetic pulse input signal to the concrete structure (S140). The electromagnetic pulse input signal is reflected from the interface of the concrete structure, and may be an electromagnetic pulse reflection signal. The GPR receiver may receive, and output to the controller, an electromagnetic pulse reflection signal (S150). Detailed embodiments may be similar to those described in FIG. 9.

The controller may derive the first moisture content of the concrete structure using the impedance of the second coil calculated using the induced voltage signal and the alternating current input signal. More specifically, the controller may calculate the impedance of the second coil using an induced voltage signal and an alternating current input signal, and for example, the impedance of the second coil may be calculated by performing fast Fourier transform on the induced voltage signal and the AC input signal. Detailed embodiments may be similar to those described in FIGS. 4 and 5.

In an example embodiment, the controller may derive the first moisture content using the real and imaginary parts of the impedance of the second coil, and detailed embodiments may be similar to those described in FIGS. 6 and 7. In another embodiment, the controller may derive the first moisture content using the phase of the impedance of the second coil, and detailed embodiments may be similar to those described in FIG. 8. In another embodiment, the controller may derive the first moisture content using all the real part, imaginary part, and phase of the impedance of the second coil.

Additionally, the controller may derive the second moisture content of the concrete structure using the electromagnetic pulse reflection signal. More specifically, the controller may calculate the speed of the electromagnetic pulse reflection signal using the time between adjacent peak values among the plurality of peak values of the electromagnetic pulse reflection signal. The controller may derive the dielectric constant using the speed of the electromagnetic pulse reflection signal, and the controller may derive the second moisture content using the calculated dielectric constant. One detailed embodiment may be similar to that described in FIG. 10.

The controller derives the final moisture content using at least one of the first moisture content and the second moisture content, and the mechanical properties of the concrete structure may be derived using the final moisture content (S160). Mechanical properties of concrete structures may include at least one of elastic modulus and compressive strength.

In an example embodiment, when both the first moisture content and the second moisture content are within the error range, the controller may derive the average of the first moisture content and the second moisture content as the final moisture content. In another embodiment, when one of the first moisture content and the second moisture content is outside the error range, the controller may derive the moisture content that is not outside the error range among the first moisture content and the second moisture content as the final moisture content.

Afterwards, the final moisture content and mechanical properties may be output to the output unit (S170). Using the printed final moisture content and mechanical properties, whether the concrete structure is leaking and the degree of leakage may be determined (S180). More specifically, if the moisture content is higher than the standard, it may be determined that a water leak has occurred, and the degree of water leakage may be determined using the moisture content value. Additionally, if the elastic modulus and/or compressive strength of the concrete structure is lower than the standard, it may be determined that a water leak has occurred.

By repeating the above operations (S100-S180), whether there is water leakage and the degree of water leakage for the entire concrete structure may be determined.

As set forth above, according to an example embodiment, a measuring apparatus for a concrete structure includes an eddy current sensor and a GPR sensor, and whether a concrete structure is leaking and the degree of leakage may be determined by measuring a moisture content and mechanical properties of concrete structures using the output of the eddy current sensor and the output of the GPR sensor. Therefore, water leakage problems may be detected early without directly evaluating a waterproofing material after the water leakage of the concrete structure has progressed to an outermost area.

The controller described herein (e.g., controller 130/630), may include one or more processor. For example, the controller may include one or more various processors such as a central processing unit (CPU), a neural processing unit (NPU), a graphic processing unit (GPU), a digital signal processor (DSP), a micro-processor, an application processor (AP), a communication processor (CP), an advanced RISC machine processor (ARM processor), a micro controller unit (MCU), a micro processing unit (MPU), a controller, and the like.

The controller 130 may be implemented with a system on chip (SoC), large scale integration (LSI) in which various processing algorithms are embedded, or implemented with a field programmable gate array (FPGA). The controller 130 may perform various functions by executing computer executable instructions stored in a memory.

When the instructions are executed by the controller, the controller may perform a function corresponding to the instructions directly or by using other components under the control of the controller. The instructions may include a code generated by a compiler or a code executable by an interpreter. A machine-readable storage medium may be provided in the form of a non-transitory storage medium. Herein, the term "non-transitory" only denotes that a storage medium does not include a signal but is tangible, and does not distinguish the case in which a data is semi-permanently stored in a storage medium from the case in which a data is temporarily stored in a storage medium.

According to an embodiment, the method according to various embodiments disclosed herein may be provided in a computer program product. A computer program product may be exchanged between a seller and a purchaser as a commodity. A computer program product may be distributed in the form of a machine-readable storage medium (e.g., compact disc read only memory (CD-ROM)) or distributed online through an application store (e.g. PlayStore™) directly between two user devices (e.g., smartphones). In the case of on-line distribution, at least a portion of the computer program product may be stored temporarily or at least temporarily in a storage medium such as a manufacturer's server, a server of an application store, or a memory of a relay server.

The output unit described herein (e.g., output unit 140/640) may be any form of interface capable of providing measurement results to a user, including without limitation a screen, a graphical user interface (GUI), one or more indicators, and a printer. The output unit may also include a transmitter configured to communicate with an external device, such as a computer, a mobile device, or a data storage device, where such communication may be wired or wireless.

While example embodiments have been illustrated and described above, it will be apparent to those skilled in the art that modifications and variations could be made without departing from the scope of the disclosure as defined by the appended claims.

What is claimed is:

1. An apparatus for measuring a concrete structure, the apparatus comprising:
- an eddy current sensor configured to contact the concrete structure;
- a ground penetrating radar (GPR) sensor configured to contact the concrete structure;
- at least one memory storing one or more instructions; and
- a controller operably connected to the eddy current sensor, the GPR sensor, and the at least one memory, wherein the one or more instructions, when executed by the controller, cause the apparatus to:
- provide a first input signal to the eddy current sensor and a second input signal to the GPR sensor,
- obtain a first moisture content of a portion of the concrete structure based on an output of the eddy current sensor,
- obtain a second moisture content of the portion of the concrete structure based on an output of the GPR sensor, and
- obtain a final moisture content of the portion of the concrete structure based on at least one of the first moisture content and the second moisture content.

2. The apparatus of claim 1, wherein the first input signal comprises an alternating current (AC) input signal, and the second input signal comprises an electromagnetic pulse input signal.

3. The apparatus of claim 2, wherein the eddy current sensor comprises a first coil and a second coil,
- wherein the first coil is configured to generate a first magnetic field based on the AC input signal, and
- wherein the one or more instructions, when executed by the controller, further cause the apparatus to detect an eddy current in the portion of the concrete structure based on an induced voltage signal generated in the second coil,
- wherein the eddy current is generated by the first magnetic field, and
- wherein the induced voltage signal is generated by the first magnetic field and a second magnetic field generated by the eddy current.

4. The apparatus of claim 3, wherein the one or more instructions, when executed by the controller, further cause the apparatus to:
- obtain an impedance of the second coil based on the induced voltage signal and the AC input signal, and
- obtain the first moisture content based on a real part of the impedance of the second coil and an imaginary part of the impedance of the second coil.

5. The apparatus of claim 3, wherein the one or more instructions, when executed by the controller, further cause the apparatus to:
- obtain an impedance of the second coil based the induced voltage signal and the AC input signal, and
- obtain the first moisture content based on a phase of the impedance of the second coil.

6. The apparatus of claim 5, wherein the one or more instructions, when executed by the controller, further cause the apparatus to:
- obtain the impedance of the second coil by performing a Fast Fourier Transform on each of the induced voltage signal and the AC input signal.

7. The apparatus of claim 2, wherein the GPR sensor comprises a GPR transmitter and a GPR receiver,
- wherein the GPR transmitter is configured to transmit the electromagnetic pulse input signal toward the portion of the concrete structure,
- wherein the GPR receiver is configured to receive an electromagnetic pulse reflection signal which is the electromagnetic pulse input signal reflected from an interface of the concrete structure.

8. The apparatus of claim 7, wherein the electromagnetic pulse reflection signal comprises a plurality of peak values, and
- wherein the one or more instructions, when executed by the controller, further cause the apparatus to:

obtain a speed of the electromagnetic pulse reflection signal based on a time between adjacent peak values among the plurality of peak values, and obtain the second moisture content based on the speed of the electromagnetic pulse reflection signal.

9. The apparatus of claim 1, wherein the one or more instructions, when executed by the controller, further cause the apparatus to:

obtain the final moisture content by averaging the first moisture content and the second moisture content.

10. The apparatus of claim 1, wherein the one or more instructions, when executed by the controller, further cause the apparatus to:

obtain the final moisture content by selecting one of the first moisture content and the second moisture content.

11. An apparatus for measuring a concrete structure, the apparatus comprising:

an eddy current sensor, the eddy current sensor comprising a first coil and a second coil;

a ground penetrating radar (GPR) sensor, the GPR sensor comprising a GPR transmitter and a GPR receiver;

at least one memory storing one or more instructions; and a controller operably connected to the eddy current sensor, the GPR sensor, and the at least one memory, wherein the one or more instructions, when executed by the controller, cause the apparatus to:

provide an alternating current (AC) input signal to the first coil to cause the first coil to generate a first magnetic field, wherein the first magnetic field generates an eddy current in the concrete structure, provide an electromagnetic pulse input signal to the GPR transmitter, receive an induced voltage signal generated by the second coil, wherein the induced voltage signal is generated in response to the first magnetic field and a second magnetic field generated by the eddy current, control the GPR transmitter to transmit the electromagnetic pulse input signal toward the concrete structure, receive, through the GPR receiver, an electromagnetic pulse reflection signal, wherein the electromagnetic pulse reflection signal is reflected from an interface of the concrete structure, obtain an impedance of the second coil based on the induced voltage signal and the AC input signal, obtain a first moisture content of a portion of the concrete structure based on the impedance of the second coil, obtain a second moisture content of the portion of the concrete structure based on the electromagnetic pulse reflection signal, obtain a final moisture content of the portion of the concrete structure based on at least one of the first moisture content and the second moisture content, and obtain mechanical properties of the portion of the concrete structure based on the final moisture content.

12. The apparatus of claim 11, wherein the one or more instructions, when executed by the controller, further cause the apparatus to:

obtain the impedance of the second coil by performing a Fast Fourier Transform on each of the AC input signal and the induced voltage signal.

13. The apparatus of claim 11, wherein the electromagnetic pulse reflection signal comprises a plurality of peak values, and wherein the one or more instructions, when executed by the controller, further cause the apparatus to:

obtain a speed of the electromagnetic pulse reflection signal based on a time between adjacent peak values among the plurality of peak values, and obtain the second moisture content based on the speed.

* * * * *